(12) United States Patent
Newman et al.

(10) Patent No.: US 6,843,107 B2
(45) Date of Patent: Jan. 18, 2005

(54) SYSTEM AND PROCESS FOR DETECTING LEAKS IN SEALED ARTICLES

(76) Inventors: John W. Newman, 1055 W. Germantown Pike, Norristown, PA (US) 19403; Steve Thayer, 1055 W. Germantown Pike, Norristown, PA (US) 19403

( * ) Notice: Subject to any disclaimer, the term of this patent is extended or adjusted under 35 U.S.C. 154(b) by 0 days.

(21) Appl. No.: 10/641,545

(22) Filed: Aug. 15, 2003

(65) Prior Publication Data
US 2004/0057043 A1 Mar. 25, 2004

Related U.S. Application Data
(60) Provisional application No. 60/406,862, filed on Aug. 29, 2002.

(51) Int. Cl.⁷ .................................................. G01M 3/34
(52) U.S. Cl. .................... 73/49.3; 356/237.1; 356/35.5; 73/49.2
(58) Field of Search .................... 356/237.1, 237.2, 356/240.1, 35.5; 250/559.19, 559.22, 559.23; 73/40, 788, 40.7, 789, 49.2, 49.3

(56) References Cited

U.S. PATENT DOCUMENTS

| | | | |
|---|---|---|---|
| 4,702,594 A | 10/1987 | Grant | |
| 4,887,899 A | 12/1989 | Hung | |
| 4,893,499 A | * 1/1990 | Layton et al. | ................ 73/49.3 |
| 5,082,366 A | 1/1992 | Tyson, II et al. | |
| 5,257,088 A | 10/1993 | Tyson, II et al. | |
| 5,263,361 A | * 11/1993 | Gates | ........................ 73/45.5 |
| 5,307,139 A | 4/1994 | Tyson, II et al. | |
| 5,361,626 A | 11/1994 | Colligan et al. | |
| 6,040,900 A | 3/2000 | Chen | |
| 6,043,870 A | 3/2000 | Chen | |
| 6,167,751 B1 | 1/2001 | Fraim et al. | |
| 6,219,143 B1 | 4/2001 | Lindsay et al. | |
| 2003/0016361 A1 | * 1/2003 | Mank et al. | ................. 356/432 |

* cited by examiner

Primary Examiner—Michael P. Stafira
Assistant Examiner—Juan D Valentin, II
(74) Attorney, Agent, or Firm—Knoble Yoshida & Dunleavy, LLC

(57) ABSTRACT

A system and method for leak testing a plurality of hermetic electronic packages of the type that have an internal chamber that is isolated from ambient conditions by a seal structure is advantageously designed to be able to calculate the leak rate of each individual device in a manner that is independent of structural manufacturing variances that typically exist within a sampling of such devices. The method preferably involves positioning a plurality of the hermetic electronic packages within a test area, and then stimulating the hermetic electronic packages with a modulated input of energy, such as by varying the ambient pressure about the devices. A property such as the physical position of one portion of a lid of each of the hermetic electronic packages is then sensed. The sensed property is one that is known to change as a first function of the modulated input of energy and also as a second function of pressure conditions within the hermetically sealed internal chamber. The first and second functions are linearly independent of each other. By comparing the stimulation of the devices to the sensed property and by discriminating using the two known functions a leak rate is determined for each individual device that is substantially independent of variances, such as differences in lid thickness that may exist between the different devices. Accordingly, an accurate determination of leak rate may be made with a minimum of calibration.

53 Claims, 3 Drawing Sheets

SYSTEM AND PROCESS FOR DETECTING LEAKS IN SEALED ARTICLES

This application claims the benefit of prov. application 60/406,862 filed on Aug. 29, 2002.

BACKGROUND OF THE INVENTION

1. Field of the Invention

This invention relates to the testing for leaks of sealed articles, such as packaging for hermetic electronic packages, including but not limited to medical implants, hybrid circuits, microwave, MEMS and photonic or fiber optic devices.

2. Description of the Related Technology

Microcircuits, laser/fiber junctions, wire, wire bonds and other components in optoelectronic devices are subject to damage from corrosion or contamination from exposure to water vapor, oxygen and other gases. This damage and the rate of corrosion of these internal components have a direct impact on the reliability and life-time of hermetic electronic packages. In today's world of telecommunication, medial implants and military High Reliability electronics, reliability less than six sigma is not acceptable. As a result, electronic devices requiring high reliability are hermetically packaged and extensively leak tested to ensure product reliability. Metal or ceramic hermetic electronic packages with soldered, welded or brazed metal lids offer both the reliability and hermeticity required for these critical devices. While current lid seam sealers provide highly reliable hermetic joints, leak testing is required to verify hermeticity and achieve the required reliability. Leak testing of sealed articles is also needed in other industries as well.

The most frequently used leak test methods in the semiconductor industry are bubble leak testing and helium mass spectroscopy. For gross leaks, the bubble method is performed by immersion of the package into a bath of perfluorocarbon liquid. Bubbles emanating from the hermetic electronic package indicate a leak. For fine leaks, a mass spectrometer is often used to detect helium leaking from hermetic electronic packages. Bubble leak testing is applicable for gross leaks only. Helium mass spectroscopy is valid only for fine leaks, smaller than about $1 \times 10E-6$ cc-atm/sec. While these methods are reliable for many semiconductor and hybrid hermetic electronic packages, bubble and helium mass spectroscopy leak testing suffer from a number of intrinsic problems when applied to fiber optic devices.

Bubble leak testing requires immersing the hermetic electronic packages in perfluorocarbon liquid heated to 125° C., necessary since the internal gas pressure inside the device must be raised high enough to generate a gas flow through the leak. The gas bubble escaping from the hermetic electronic package is observed by the operator viewing through a window in the side of the illuminated tank. Testing at lower than optimal temperatures may not increase the gas pressure inside the hermetic electronic package sufficiently, resulting in a significant loss of sensitivity. Gross leaks can be missed. Unfortunately, for most of the adhesives and epoxies used for bonding laser devices, fiber optic cable terminations and other components inside the device, the required 125° C. temperature approaches or exceeds the glass transition temperature. Exposures to the required 125° C. temperature will severely damage most fiber optic devices. In addition, for many fiber optic devices, the intrusion of perfluorocarbon liquid into the cavity, if it leaks, causes severe contamination. In many instances, devices failing gross leak bubble testing are considered as scrap since cleaning the laser/fiber junction is nearly impossible. Bubble leak testing can also contaminate polished fiber optic cable ends on hermetic electronic packages with pigtails. Finally, for many hermetic electronic packages without fiber pigtails, with lenses or optical windows in the side of the hermetic electronic package, contamination can easily occur during bubble leak testing again causing expensive rework or scrap.

Helium mass spectroscopy detects helium emanating from inside the hermetic electronic package. The test can be set up two ways. First, a specified amount of helium can be sealed into the hermetic electronic package by having a controlled concentration of helium in the seam sealer dry box. Second, the hermetic electronic packages can be bombed, by placing the devices in a chamber with helium at 50–70 psi for a period of time up to eight hours depending on hermetic electronic package internal volume. Helium will diffuse into leaking hermetic electronic packages and be detected later when it diffuses out of the hermetic electronic package in the vacuum test cell of the mass spectrometer. Sealing the lid in a 90% dry nitrogen and 10% helium atmosphere has problems in that the helium concentration may change over time at the location of the lid seal welder within the dry box. This can substantially influence any subsequent leak test data by changing the concentration of helium inside the hermetic electronic package at the time of sealing. Testing must be performed immediately after bombing or sealing in the helium during the lid attachment.

Due to the very fast helium migration rate through gross leaks, the amount of helium detected may be extremely small or non-existent by the time the device is tested in a mass spectrometer. Whatever helium may have been present might be gone, allowing gross leaking devices to be passed. In order to ensure hermetic electronic packages are not leaking over the full range from the "no lid condition," gross leak through fine leak using conventional leak test methods, multiple techniques must be used. Helium mass spectroscopy alone cannot verify hermeticity.

Another problem for many fiber optic devices or any device using ceramic or organic materials is caused by helium absorption by fiber armor cladding and boots followed by subsequent de-gassing during the helium leak testing process when the hermetic electronic package is subjected to a vacuum. This helium is detected by the mass spectrometer and reported as a false reading. Fiber cladding, boots and ceramic couplings are also strong helium absorbers and can lead to false leak test readings. Helium bake out procedure prior to leak testing can damage devices and add further leak test errors. These resulting false calls can lead to scrapping parts or needless and very expensive rework. Highly skilled operators and stringent adherence to procedures is critical. Even then, mass spectrometer leak test results are not highly repeatable sometimes varying by an order of magnitude. When helium is detected during batch leak testing, the operator can not determine from one test if all of the devices or just one are leaking. The population must be divided in half and retested until the individual leaking hermetic electronic package(s) are located. As it may be imagined, this is a costly and time-consuming process.

Finally, conventional leak test methods are difficult to automate, which is the key to lowering manufacturing costs for fiber optic devices. And while leak testing measures the quality of the lid seam sealing operation, conventional methods can not provide a means of process control due to the time delay between lid welding and reporting leak test results.

Optical Leak Testing was first developed by one of the present inventors and a colleague several years ago to leak test computer modules. U.S. Pat. No. 5,307,139 to Tyson et al. describes an early embodiment of this type of testing. An early application of this technology was to test ceramic hermetic electronic packages in which ceramic lids and glass frit seals had cracked during wave soldering.

The rapid advances in the 1990's of computers, digital CCD video cameras and the solid state, single frequency laser emitting visible light led to the development of the current automated optical leak test systems based on digital electronic holography interferometry. These production systems are not only easy to use but also have demonstrated greatly increased leak sensitivity to 2×10E−9 cc-atm/sec., at least a two order of magnitude increase. Optical Leak Test technology marries electronic digital holography, a test chamber with computer controlled precision helium pressurization system and software to determine leak rates from the analysis of hermetic electronic package lid deformation measurements, instantaneous lid velocity and changes in lid velocity over time.

Leak testing hermetic electronic package entails loading the devices, usually in a tray or carrier used for the lid sealing operation, into the open chamber door. The door is closed and the test initiated. The test chamber is purged of air and flushed with helium, then pressurized to the test pressure which varies by hermetic electronic package size, being careful not exceed the maximum allowable for the device. Gross leaking devices are detected through measurement of lid movement during a change in chamber pressure. A negative response indicates rapid equalization of the gas pressure between the cavity of the device and the test chamber pressure. Fine leak devices are detected by a change in lid contour during a period of stable elevated chamber pressure. Leaking devices will be detected by a gradual change in the out-of-plane contour of the lid. In practice, up to 200 devices may be tested at once with leak rates reported on each individual hermetic electronic package.

Optical leak testing of hermetically sealed hermetic electronic packages is accordingly based on observation of hermetic electronic package lid deflection over time. While it provides many advantages over alternative techniques, it requires time-consuming initial calibration for each type of hermetic electronic package using sample hermetic electronic packages with known helium leak rates.

Another problem that exists in conventional optical leak testing systems is that it assumes all samples of a specific hermetic electronic package type have the same mechanical stiffness. In practice, hermetic electronic package lid stiffness can vary slightly from hermetic electronic package to hermetic electronic package due to small variations in material thickness and slight variations in manufacturing process control. While such minute variations in lid stiffness are of no concern mechanically, they can be a significant source of error in optical leak testing. It is clear that a need exists for an improved system and process for leak testing a hermetically sealed hermetic electronic package that requires less calibration effort and that provides a more accurate indication of the leak rate of hermetically sealed hermetic electronic package than conventional optical leak testing.

SUMMARY OF THE INVENTION

Accordingly, it is an object of the invention to provide an improved system and process for leak testing a hermetically sealed hermetic electronic package that requires less calibration effort and that provides a more accurate indication of the leak rate of hermetically sealed hermetic electronic packages than conventional optical leak testing.

In order to achieve the above and other objects of the invention, a method of leak testing a hermetic electronic package of the type that has an internal chamber that is isolated from ambient conditions by a seal structure includes, according to a first aspect of the invention, steps of stimulating the hermetic electronic package with a modulated input of energy; sensing a property of the hermetic electronic package that changes as a first function of the modulated input of energy and a second function of pressure conditions within the hermetically sealed internal chamber, the first and second functions being linearly independent; and determining a leak rate of the hermetic electronic package based on the known modulated input of energy and the sensed property, said determination being performed in reliance on the linear independence of the first and second functions in such a manner that it is substantially independent of structural manufacturing variances of the hermetic electronic package that are unrelated to the integrity of the seal.

According to a second aspect of the invention, a method of leak testing a plurality of hermetic electronic packages of the type that have an internal chamber that is isolated from ambient conditions by a seal structure includes steps of positioning a plurality of hermetic electronic packages within a test area; stimulating the hermetic electronic packages with a modulated input of energy; sensing a property of each of the hermetic electronic packages that changes as a first function of the modulated input of energy and a second function of pressure conditions within said hermetically sealed internal chamber, the first and second functions being linearly independent; and determining a leak rate of each hermetic electronic package based on the known modulated input of energy and the sensed property, said determination being performed in reliance on the linear independence of the first and second functions in such a manner that it is substantially independent of structural manufacturing variances between the individual hermetic electronic packages that are unrelated to the integrity of the seal.

According to third aspect of the invention, an apparatus for leak testing a hermetic electronic package of the type that has an internal chamber that is isolated from ambient conditions by a seal structure includes energy input structure for stimulating the hermetic electronic package with a modulated input of energy; sensing structure for sensing a property of the hermetic electronic package that changes as a first function of the modulated input of energy and a second function of pressure conditions within said hermetically sealed internal chamber, said first and second functions being linearly independent; and determining structure for determining a leak rate of the hermetic electronic package based on the known modulated input of energy and the sensed property, said determining structure being constructed and arranged to make such a determination in reliance on the linear independence of said first and second functions in such a manner that it is substantially independent of structural manufacturing variances of the hermetic electronic package that are unrelated to the integrity of the seal. An apparatus for leak testing a plurality of hermetic electronic packages of the type that have an internal chamber that is isolated from ambient conditions by a seal structure includes, according to a fourth aspect of the invention, positioning structure for positioning a plurality of hermetic electronic packages within a test area; energy input structure for stimulating the hermetic electronic packages with a modulated input of energy; sensing structure for sensing a property of each of the hermetic electronic packages that changes as a first function of the modulated input of energy and a second function of pressure conditions within the hermetically sealed internal chamber, the first and second functions being linearly independent; and determining structure for determining a leak rate of each hermetic electronic package based on the known modulated input of energy and the sensed property, the determination being performed in reliance on the linear independence of said first and second functions in such a manner that it is substantially independent of structural manufacturing variances between the individual hermetic electronic package that are unrelated to the integrity of the seal.

A method of leak testing a sealed article of the type that has an internal chamber that is isolated from ambient conditions by a seal structure according to a fifth aspect of the invention includes steps of stimulating the sealed article with a modulated input of energy; sensing a property of the sealed article that changes as a first function of the modulated input of energy and a second function of pressure conditions within said sealed article, the first and second functions being linearly independent; and determining a leak rate of the sealed article based on the known modulated input of energy and the sensed property, this determination being performed in reliance on the linear independence of the first and second functions in such a manner that it is substantially independent of structural manufacturing variances of the sealed article that are unrelated to the integrity of the seal.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT(S)

Figure 1:
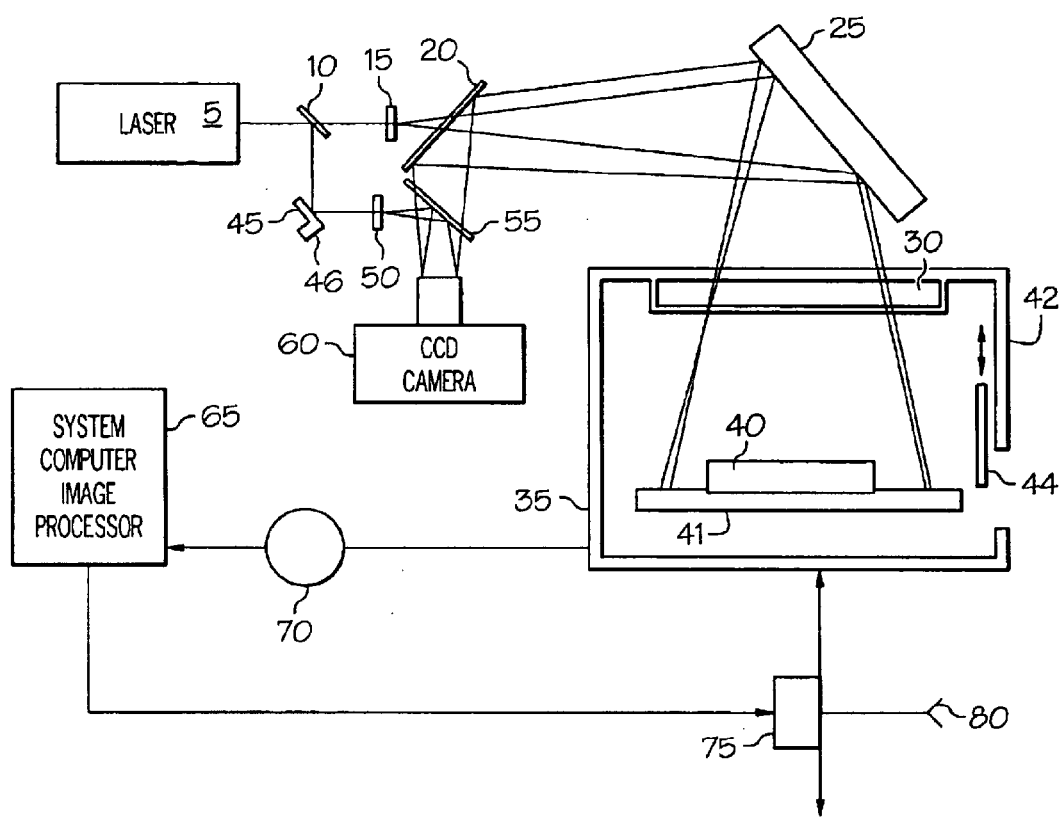
FIG. 1 is a schematic diagram depicting a first embodiment of the invention.

Referring now to the drawings, wherein like reference numerals designate corresponding structure throughout the views, and referring in particular to FIG. 1, an apparatus for leak testing a plurality of hermetically sealed electronic devices according to the first embodiment of the invention includes a housing 42 and a transparent glass or plastic window 30 that together define a pressure test cell 35 in order to form a pressure tight vessel. Helium control valve 75 allows pressurized helium gas 80 to be admitted to the test cell 35 or for helium within the test cell 35 to be vented, reducing the pressure within the test cell 35 to atmospheric pressure. The helium pressure inside the test cell 35 is measured with a precision, temperature compensated electronic pressure sensor 70. A sealed door 44 in test cell 35 may be opened to allow one or more hermetically sealed electronic devices 40 to be placed onto a test tray support platform to position the devices in the test cell window 30. Advantageously, the hermetically sealed electronic devices may be tested in situ according to the invention after attachment to a printed circuit board 41. This ensures that any degradation of seal integrity as a result of the soldering process by which an electronic device 40 is attached to the printed circuit board 41 may be detected.

The change in the out-of-plane position of the surface of the hermetic electronic packages, such as the welded or soldered lid is observed by an interferometric apparatus. The interferometric apparatus shown in FIG. 1 is a digital phase stepping holographic interferometer and includes a Laser 5, a beam splitter 10 an expansion lens 15 to expand the illumination laser beam onto the test hermetically sealed devices by way of mirror 25 and test cell window 30. Laser light reflected from the lids of the test devices passes back through test cell window 30 and mirror 25. The reflected light then reflects from beam splitter 20 and passes through beam splitter 55 in the objective lens of a digital CCD video camera 60. This wave front of reflected laser light is mixed interferometrically with a pure reference beam wave front Laser 5 that arrives at the focal plane of the CCD camera lens by way of beam splitter 10, mirror 45, expansion lens 50 and beam splitter 55.

The system computer contains the operating program, I/O to measure the output of the precision pressure sensor 70 reading the helium pressure inside the test cell and to operate the three way helium control valve 75. In addition, the system computer contains a video frame grabber card and memory to store video interferograms or output images from the CCD camera. In addition the system computer controls the position of a mirror 45 by way of a piezoelectric phase stepper device 46.

Figure 2:
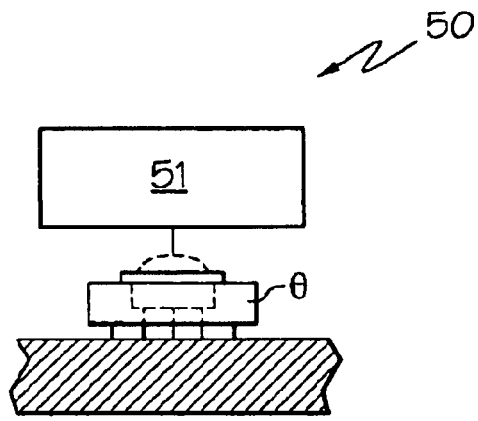
FIG. 2 is a schematic diagram depicting a second embodiment of the invention.

FIG. 2 is a schematic depiction of a second embodiment of the invention, which is identical in its use to the previously described embodiments, with the exception that movement of the top surface of microchip hermetic electronic package 9 is sensed by an alternate automated sensor 50, which preferably includes a capacitance probe 51. Probes using this technology are well known and are commercially available.

Figure 3:
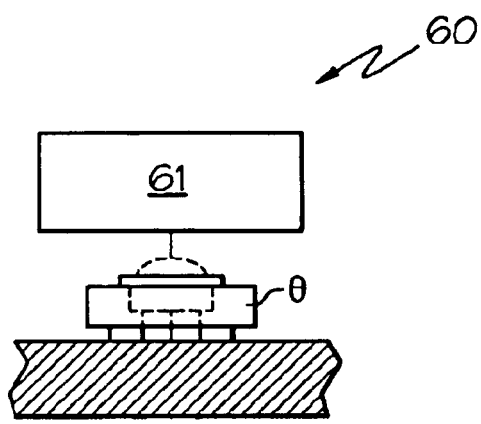
FIG. 3 is a schematic diagram depicting a third embodiment of the invention.

Referring now to FIG. 3 a third embodiment of the invention that yet a different alternative automated sensor 60 for measuring movement of the top surface of the microchip hermetic electronic package 9, which preferably utilizes an eddy current probe 61. Sensors of this type are also well known and are commercially available.

Figure 4:
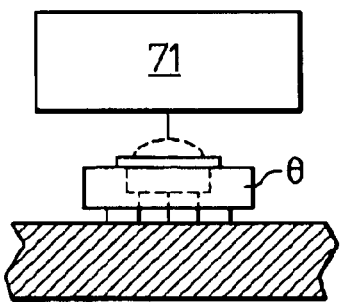
FIG. 4 is a schematic diagram depicting a fourth embodiment of the invention.

Looking now to FIG. 4, a fourth embodiment of the invention utilizes an automated sensor 70 that preferably is a laser triangulation probe. Sensors of this type are also well known and are commercially available.

It has been found that an accurate determination of the leak rate, in both the gross leak and fine leak tests, depends on three parameters other than the measured rate of change of lid deformation. These parameters are 1) the amount of the test pressure, 2) the stiffness of the lid, and 3) the size of the internal cavity of the hermetic electronic package.

According to one important aspect of the invention, to eliminate the problem of lid stiffness variation a new test methodology has been developed to solve for internal hermetic electronic package pressure change directly. The algorithm employed solves for internal pressure change and lid stiffness simultaneously and also calculates the leak rate for the device package.

For the purposes of modeling the change in internal hermetic electronic package pressure we assume that the chamber has been pressurized to some working pressure greater than one atmosphere and that the chamber and hermetic electronic package s have reached thermal equilibrium. During the course of the test, the hermetic electronic package is stimulated with a modulated input of energy, preferably by modulating the chamber pressure slowly about the working pressure. In the embodiment of FIG. 1, this modulation is controlled and monitored by the computer 65, which controls operation of a pump or compressor and further monitors the pressurization of the test cell 35 by means of a pressure sensor 70. Simultaneously, a property of the hermetic electronic package 40 that changes as a first function of the modulated input of energy and also as a second function, linearly independent of the first function, of pressure conditions within the hermetically sealed internal chamber 35 is sensed and is monitored by computer 65 as well. In the preferred embodiment, this property is the displacement of a single location on the lid of the hermetic electronic package 40, although it is to be understood that other properties that likewise are affected by similar linearly independent functions could also be utilized within the spirit and scope of the invention. As will be described in detail below, the leak rate of the hermetic electronic package 40 may then the determined based upon the known modulated input of energy, the sensed property and the known approximate volume of the interior of the hermetic electronic package 40.

The basic equation governing hermetic electronic package lid deflection may be expressed as:

$$d(t)=c_0(P_c(t)-P_p)-P_p(t) \tag{1}$$

Where:
$d(t)$=observed lid deflection.
$c_0$ hermetic electronic package lid stiffness (um/psi).
$P_c$=observed change in chamber pressure.
$P_p$=change in internal hermetic electronic package pressure.

It is assumed that the change in internal hermetic electronic package pressure during the course of the test can be approximated by a $2^{nd}$ order polynomial of the form:

$$P_p(t)=c_1 t^2+c_2 t \tag{2}$$

The choice of equation (2) to represent the change of internal pressure is based on past experience and observation. The constant term in the polynomial has been dropped to enforce the boundary condition of zero internal pressure change at the start of the test.

It is important to note that in order to differentiate lid deflection due to chamber pressure fluctuations $P_c(t)$ from lid deflection due to changes in internal hermetic electronic package pressure $P_p(t)$, the two components must be linearly independent. For this reason a non-linear, sinusoidal pressure modulation function as been used for $P_c(t)$. By substituting equation (2) into equation (1) we get:

$$d(t)=c_0(P_c(t)-c_1 t^2-c_2 t) \tag{3}$$

If the preceding condition of linear independence has been met, the three unknown parameters in equation (3) can be determined using standard linear estimation techniques.

Figure 5:
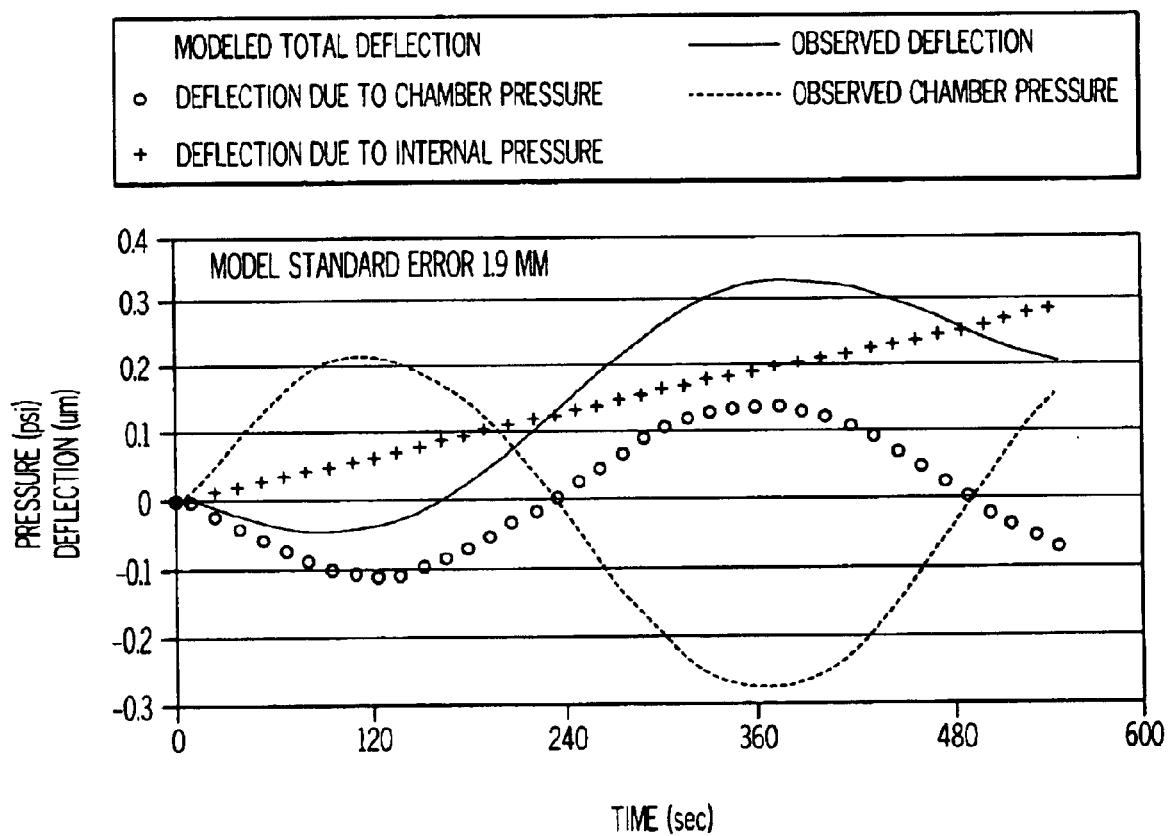
FIG. 5 is a graphic representation depicting a method that is performed according to the preferred embodiment of the invention.

FIG. 5 presents a typical example of the leak deflection model. The data shown in FIG. 5 were generated by a hermetic electronic package that tested at $5.6 \times 10^{-7}$ atm-cc/sec using traditional helium mass spectrometry leak testing. As can be seen in the figure, the modeled total deflection closely fits the observed total deflection. In addition to the total modeled lid deflection, the plot shows the component of total modeled deflection due to chamber pressure modulation and the component due to internal pressure change.

Once the leak deflection model has been solved, the actual change in internal hermetic electronic package pressure is found by evaluating (3) using the total test time$^t$. With the change in internal hermetic electronic package pressure known, the measured helium leak rate can be calculated using equation (4). Note that the $\Delta p$ terms in equation (4) represent the difference between the chamber pressure and the internal hermetic electronic package pressure.

$$\Delta p_1 = \Delta p_i e^{-Lt/V} \tag{4}$$

Where:
$\Delta p_i$=initial pressure difference (atm).
$\Delta p_1$=final pressure difference (atm).
V=internal hermetic electronic package volume (cc).
t=length of test (sec).

For the current example, the computed change in internal hermetic electronic package pressure was $3.76 \times 10^{-2}$ atm, the chamber working pressure was 3.68 atm, and the test time was 556 sec. The internal hermetic electronic package volume was estimated at 0.1 cc.

It is assumed that the hermetic electronic package enters the test chamber with an internal pressure of 1 atm. The test procedure, however, requires a period of stabilization time at the start of each test. During this stabilization period the hermetic electronic packages are exposed to helium at the test working pressure. Accordingly, the pressure differences ($\Delta p$) must be adjusted to account for helium leaking into the hermetic electronic package during the stabilization period. This is a simple adjustment to make since the leak rate in atm/sec has already been determined and the stabilization time is known.

Using the previously listed test parameters and the computed internal pressure change of $3.76 \times 10^{-2}$ atm, equation (4) yields a measured leak rate of $2.53 \times 10^{-6}$ atm-cc/sec. Finally, the measured leak rate is converted to the true leak rate using equation (5)

$$L=R/p_w \tag{5}$$

Where:
L=true leak rate (atm-cc/sec).
R=measured leak rate (atm-cc/sec).
$p_W$=chamber working pressure (atm).

With a chamber working pressure of 3.68 atm, the true leak rate for the example hermetic electronic package works out to $6.88 \times 10^{-7}$ atm-cc/sec. This result agrees reasonably well with the previously stated helium leak test result $5.6 \times 10^{-7}$ atm-cc/sec. Further, the true leak rate determined using the present invention is intrinsically the helium leak rate for the package completely unaffected by absorption and emission of helium by ceramics or organic materials. Uniquely, devices soldered on circuit boards may be leak tested with no loss in accuracy or sensitivity.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A method of leak testing a hermetic electronic package of the type that has an internal chamber that is isolated from ambient conditions by a seal structure, comprising steps of:

stimulating the hermetic electronic package with a non-linear modulated input of energy;

sensing a property of the hermetic electronic package that changes as a first function of the modulated input of energy and a second function of pressure conditions within said hermetically sealed internal chamber, said first and second functions being linearly independent; and determining a leak rate of the hermetic electronic package based on the known modulated input of energy and the sensed property, said determination being performed in reliance on the linear independence of said first and second functions in such a manner that it is substantially independent of structural manufacturing variances of the hermetic electronic package that are unrelated to the integrity of the seal.

2. A method of leak testing a hermetic electronic package according to claim 1, wherein said step of stimulating the hermetic electronic package comprises modulating ambient conditions about the hermetic electronic package.

3. A method of leak testing a hermetic electronic package according to claim 2, wherein said step of stimulating the hermetic electronic package comprises modulating ambient pressure conditions about the hermetic electronic package.

4. A method of leak testing a hermetic electronic package according to claim 1, wherein said step of sensing a property of the hermetic electronic package comprises sensing a position of at least one portion of said hermetic electronic package.

5. A method according to claim 4, wherein said hermetic electronic package includes a lid portion and said step of measuring a position of at least one portion of the hermetic electronic package comprises measuring a position of at least one location on said lid portion.

6. A method according to claim 4, wherein said step of measuring a position of at least one portion of said hermetic electronic package is performed with an automated sensor.

7. A method according to claim 6, wherein said automated sensor comprises a laser interferometer.

8. A method according to claim 6, wherein said automated sensor comprises a capacitance probe.

9. A method according to claim 6, wherein said automated sensor comprises an eddy current probe.

10. A method according to claim 6, wherein said automated sensor comprises a laser triangulation probe.

11. A method according to claim 1, wherein said step of determining the leak rate comprises discriminating between variation of said property according to said first function and variation of said property according to said second function.

12. A method according to claim 1, wherein said hermetic electronic package is tested in situ while attached to a printed circuit board.

13. A method of leak testing a plurality of hermetic electronic packages of the type that have an internal chamber that is isolated from ambient conditions by a seal structure, comprising steps of:

positioning a plurality of hermetic electronic packages within a test area;

stimulating the hermetic electronic packages with a non-linear modulated input of energy;

sensing a property of each of the hermetic electronic packages that changes as a first function of the modulated input of energy and a second function of pressure conditions within said hermetically sealed internal chamber, said first and second functions being linearly independent; and determining a leak rate of each hermetic electronic package based on the known modulated input of energy and the sensed property, said determination being performed in reliance on the linear independence of said first and second functions in such a manner that it is substantially independent of structural manufacturing variances between the individual hermetic electronic packages that are unrelated to the integrity of the seal.

14. A method of leak testing a plurality of hermetic electronic packages according to claim 13, wherein said step of stimulating the hermetic electronic packages comprises modulating ambient conditions about the hermetic electronic packages.

15. A method of leak testing a plurality of hermetic electronic packages according to claim 14, wherein said step of stimulating the hermetic electronic packages comprises modulating ambient pressure conditions about the hermetic electronic packages.

16. A method of leak testing a plurality of hermetic electronic packages according to claim 13, wherein said step of sensing a property of each of the hermetic electronic packages comprises sensing a position of at least one portion of said hermetic electronic package.

17. A method according to claim 16, wherein said hermetic electronic package includes a lid portion and said step of measuring a position of at least one portion of each hermetic electronic package comprises measuring a position of at least one location on each said lid portion.

18. A method according to claim 16, wherein said step of measuring a position of at least one portion of each hermetic electronic package lid is performed with an automated sensor.

19. A method according to claim 18, wherein said automated sensor comprises a laser interferometer.

20. A method according to claim 18, wherein said automated sensor comprises a capacitance probe.

21. A method according to claim 18, wherein said automated sensor comprises an eddy current probe.

22. A method according to claim 18, wherein said automated sensor comprises a laser triangulation probe.

23. A method according to claim 13, wherein said step of determining the leak rate comprises discriminating between variation of said property according to said first function and variation of said property according to said second function.

24. A method according to claim 13, wherein said hermetic electronic package is tested in situ while attached to a printed circuit board.

25. An apparatus for leak testing a hermetic electronic package of the type that has an internal chamber that is isolated from ambient conditions air by a seal structure, comprising:

energy input means for stimulating the hermetic electronic package with a non-linear modulated input of energy;

sensing means for sensing a property of the hermetic electronic package that changes as a first function of the modulated input of energy and a second function of pressure conditions within said hermetically sealed internal chamber, said first and second functions being linearly independent; and determining means for determining a leak rate of the hermetic electronic package based on the known modulated input of energy and the sensed property, said determining means being constructed and arranged to make such a determination in reliance on the linear independence of said first and second functions in such a manner that it is substantially independent of structural manufacturing variances of the hermetic electronic package that are unrelated to the integrity of the seal.

26. An apparatus for leak testing a hermetic electronic package according to claim 25, wherein said energy input means comprises means for modulating ambient pressure conditions about the hermetic electronic package.

27. An apparatus for leak testing a hermetic electronic package according to claim 26, wherein said sensing means is constructed and arranged to sense a position of at least one portion of said hermetic electronic package.

28. An apparatus for leak testing a hermetic electronic package according to claim 27, wherein said hermetic electronic package includes a lid portion and wherein said sensing means is constructed and arranged to measure a position of at least one location on said lid portion.

29. An apparatus for leak testing a hermetic electronic package according to claim 27, wherein said sensing means comprises an automated sensor.

30. An apparatus for leak testing a hermetic electronic package according to claim 27, wherein said sensing means comprises a laser interferometer.

31. An apparatus for leak testing a hermetic electronic package according to claim 27, wherein said sensing means comprises a capacitance probe.

32. An apparatus for leak testing a hermetic electronic package according to claim 27, wherein said sensing means comprises an eddy current probe.

33. An apparatus for leak testing a hermetic electronic package according to claim 27, wherein said automated sensor comprises a laser triangulation probe.

34. An apparatus for leak testing a plurality of hermetic electronic packages of the type that have an internal chamber that is isolated from ambient conditions air by a seal structure, comprising:

positioning means for positioning a plurality of hermetic electronic packages within a test area;

energy input means for stimulating the hermetic electronic packages with a non-linear modulated input of energy;

sensing means for sensing a property of each of the hermetic electronic packages that changes as a first function of the modulated input of energy and a second function of pressure conditions within said hermetically sealed internal chamber, said first and second functions being linearly independent; and determining means for determining a leak rate of each hermetic electronic package based on the known modulated input of energy and the sensed property, said determination being performed in reliance on the linear independence of said first and second functions in such a manner that it is substantially independent of structural manufacturing variances between the individual hermetic electronic package that are unrelated to the integrity of the seal.

35. An apparatus for leak testing a plurality of hermetic electronic package according to claim 34, wherein said energy input means comprises means for modulating ambient pressure conditions about the hermetic electronic packages.

36. An apparatus for leak testing a plurality of hermetic electronic packages according to claim 35, wherein said sensing means is constructed and arranged to sense a position of at least one portion of each of said hermetic electronic packages.

37. An apparatus for leak testing a plurality of hermetic electronic packages according to claim 36, wherein each of said hermetic electronic packages includes a lid portion and wherein said sensing means is constructed and arranged to measure a position of at least one location on each of said lid portions.

38. An apparatus for leak testing a plurality of hermetic electronic packages according to claim 36, wherein said sensing means comprises an automated sensor.

39. An apparatus for leak testing a plurality of hermetic electronic packages according to claim 36, wherein said sensing means comprises a laser interferometer.

40. An apparatus for leak testing a plurality of hermetic electronic packages according to claim 36, wherein said sensing means comprises a capacitance probe.

41. An apparatus for leak testing a plurality of hermetic electronic packages according to claim 36, wherein said sensing means comprises an eddy current probe.

42. An apparatus for leak testing plurality of hermetic electronic packages according to claim 36, wherein said automated sensor comprises a laser triangulation probe.

43. A method of leak testing a sealed article of the type that has an internal chamber that is isolated from ambient conditions by a seal structure, comprising steps of:

stimulating the sealed article with a non-linear modulated input of energy;

sensing a property of the sealed article that changes as a first function of the modulated input of energy and a second function of pressure conditions within said sealed article, said first and second functions being linearly independent; and determining a leak rate of the sealed article based on the known modulated input of energy and the sensed property, said determination being performed in reliance on the linear independence of said first and second functions in such a manner that it is substantially independent of structural manufacturing variances of the sealed article that are unrelated to the integrity of the seal.

44. A method of leak testing a sealed article according to claim 43, wherein said step of stimulating the sealed article comprises modulating ambient conditions about the sealed article.

45. A method of leak testing a hermetic electronic package according to claim 44, wherein said step of stimulating the sealed article comprises modulating ambient pressure conditions about the sealed article.

46. A method of leak testing a sealed article according to claim 43, wherein said step of sensing a property of the sealed article comprises sensing a position of at least one portion of said sealed article.

47. A method according to claim 46, wherein said sealed article includes a lid portion and said step of measuring a position of at least one portion of the sealed article comprises measuring a position of at least one location on said lid portion.

48. A method according to claim 46, wherein said step of measuring a position of at least one portion of said sealed article is performed with an automated sensor.

49. A method according to claim 48, wherein said automated sensor comprises a laser interferometer.

50. A method according to claim 48, wherein said automated sensor comprises a capacitance probe.

51. A method according to claim 48, wherein said automated sensor comprises an eddy current probe.

52. A method according to claim 48, wherein said automated sensor comprises a laser triangulation probe.

53. A method according to claim 43, wherein said step of determining the leak rate comprises discriminating between variation of said property according to said first function and variation of said property according to said second function.

* * * * *